(12) United States Patent
Patton et al.

(10) Patent No.: US 7,157,059 B1
(45) Date of Patent: Jan. 2, 2007

(54) REDUCTION DEVICE FOR NITRATE DETERMINATION

(75) Inventors: Charles Johnston Patton, Evergreen, CO (US); Peter Freeman Rogerson, Golden, CO (US)

(73) Assignee: The United States of America as represented by the Secretary of the Interior, Washington, DC (US)

( * ) Notice: Subject to any disclaimer, the term of this patent is extended or adjusted under 35 U.S.C. 154(b) by 667 days.

(21) Appl. No.: 10/251,696

(22) Filed: Sep. 18, 2002

(51) Int. Cl.
*B01J 8/18* (2006.01)
*B01D 47/00* (2006.01)
*B01D 47/16* (2006.01)
*B01F 3/04* (2006.01)
*G01N 15/06* (2006.01)

(52) U.S. Cl. ........................ 422/139; 261/94; 261/100; 261/103; 261/123; 422/68.1; 422/202

(58) Field of Classification Search ................ 436/110, 436/169; 422/68.1, 202; 261/94, 100, 103, 261/123; 502/527.19
See application file for complete search history.

(56) References Cited

U.S. PATENT DOCUMENTS

| 4,192,714 A | * | 3/1980 | Vachon ........................ 376/220 |
| 5,300,441 A | * | 4/1994 | Fujinari et al. .............. 436/110 |
| 5,858,792 A | * | 1/1999 | Fanning et al. ................ 436/52 |
| 6,030,520 A | * | 2/2000 | Dziewinski et al. ........ 205/771 |

OTHER PUBLICATIONS

Gordon et al, A Suggested Protocol for Continuous Flow Automated Analysis of Seawater Nutrients in the WOCE Hydrographic Program and the Joint Global Ocen Fluxes Study, Nov. 4 1993, OSU Coll. of Oc. Descriptive Chem. Oc. Grp. Tech, p. 32-37.*
M. P. Stainton, Simple Efficient Reduction Column for Use in the Automated Determination of Nitrate in Water, Sep. 1974, Analytical Chemistry, vol. 48 No. 11, 1515.*
Raymond B. Willis and Claude E. Gentry, Automated Method for Determining Nitrate and Nitrite in Water and Soil Extracts, 1987, Commun. in soil sci. plant anal., 18(6), 625-636.*
Raymond B. Willis, Reduction Column for Automated Determination of Nitrate and Nitrite in Water, 1980, Analytical Chemistry, 52, 1377-1379.*
Article "Simple, Efficient Reduction Column for Use in the Automated Determination of Nitrate in Water", by M.P. Stainton, Analytical Chemistry, vol. 46, No. 11, Sep. 1974, p. 1618.
Article "Reduction Column for Automated Determination of Nitrate and Nitrite in Water", by Raymond B. Willis, Anal. Chem. 1988, 52, 1976, pp. 1376-1377.
Article "Automated Method for determining Nitrate and Nitrite in Water and soil Extracts", by Raymond B. Willis and Claude E. Gentry, Commun in Soil Sci Plant Anal, 18(6), 625-636 (1987).

* cited by examiner

*Primary Examiner*—Jill Warden
*Assistant Examiner*—Keri A. Moss
(74) *Attorney, Agent, or Firm*—Mark Homer; Joan Gilsdorf

(57) ABSTRACT

A nitrate reduction device has a cadmium structure forming a plurality of longitudinal channels within a flow chamber, which may be formed by a plurality of wires. The device is used to reduce nitrate to a final nitrite product for analysis.

17 Claims, 7 Drawing Sheets

(Cross-section view A-A)

≈ 4.8 mm o.d. x 3.2 mm id
FEP Teflon tubing

≈0.8 mm (95/5)
cadmium/silver alloy wire

| PROVIDING A NITRATE REDUCTION DEVICE WITH A REACTOR HAVING A FLOW CHAMBER HAVING A FIRST END FOR RECEIVING A NITRATE SAMPLE AND A PLURALITY OF CADMIUM CONTAINING WIRES LOCATED WITHIN THE FLOW CHAMBER | 100 |
|---|---|

| INPUTTING NITRATE SAMPLE INTO THE FLOW CHAMBER | 102 |
|---|---|

| CYCLING THE NITRATE SAMPLE WITHIN THE FLOW CHAMBER IN A MANNER EFFECTIVE TO REDUCE THE NITRATE TO NITRITE | 104 |
|---|---|

REDUCTION DEVICE FOR NITRATE DETERMINATION

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention includes a nitrate reduction device for use on environmental monitors. The nitrate reduction device has a flow chamber containing a cadmium structure forming a plurality of longitudinal channels within the flow chamber. The cadmium structure may be formed by a plurality of cadmium containing wires.

2. Brief Description of the Related Art

Nitrite in natural water samples typically is determined colorimetrically using Griess reaction reagents, such as sulfanilamide and N-(1-Naphthyl)ethylenediamine. Equivalent specific and sensitive colorimetric reagents for nitrate determinations are not available. Therefore, nitrate is frequently reduced to nitrite prior to analytical determinations. Reduction of nitrate to nitrite with zinc, hydrazine, bacterially derived nitrate reductase, and ultraviolet radiation has been reported. Additionally, cadmium has been used in packed bed, single wire-in-tube, and open tubular configurations for nitrate reductions.

Zinc provides a problematic reducing agent in that it is overly reactive resulting in reduction of nitrate to other species in addition to nitrite. Reduction of nitrate to nitrite by hydrazine is kinetically unfavorable and difficult to control. Bacterially derived nitrate reductase becomes inactive in air-saturated solutions and requires a hazardous cofactor. Ultraviolet radiation is not kinetically favored and difficult to control. Additionally ultraviolet radiation has power requirements to an ultraviolet lamp that may become prohibitive for remote applications.

For cadmium reduction systems, out gassing of samples and reagent creates void areas in granular cadmium packed bed reactors that lower reactivity. Resistance to flow (back pressure) in packed-bed, granular cadmium reactor systems can also be problematic. Additionally, the dissolution of cadmium granules that occurs as the granules react with nitrate and dissolved oxygen causes progressively increasing void volumes at the head of the reactor, adversely affecting reduction efficiency. Both the single wire-in-tube and the open-tubular reactor are immune to void areas and have lower back pressures, but have lower reactive surface-to-volume characteristics.

Single wire-in-tube cadmium reactors have been disclosed in Stainton, M. P., *Anal. Chem.*, 1974, 46, 1616 ("Stainton Article"); Willis, R. B., *Anal. Chem.*, 1980, 52, 1377–1379 ("Willis Article"); and Willis, R. B. and Gentry, C. E., *Commun. In Soil Sci. Anal.*, 1987, 18, 625–636 ("Willis et al. Article"). The Stainton Article discloses a 1-meter length $\frac{1}{32}$-inch i.d. Teflon tubing threaded with a 1-meter length of 1 millimeter diameter (sic) cadmium wire. The Willis Article discloses the use of a wire made of an alloy of 95% cadmium and 5% silver. The Willis et al. Article also discloses the use of a cadmium-silver wire. As such, none of these references address the need for high reactive surface-to-volume characteristics.

For any passive-wall tubular, active-metal, nitrate reduction system of volume, V, with length, L, and diameter, D, the speed and completeness of reduction, referred to as reduction efficiency in discussions that follow, increase as the surface area of the active metal in contact with the nitrate-containing solution increases. In the case of granular-cadmium, packed-bed reactor systems, reduction efficiency increases as the size of cadmium granules decreases. Aforementioned operability problems, including increased back pressure, increases as the size of cadmium granules decrease. In the case of single-wire-in-tube systems, high reduction efficiency is achieved only when the diameter of the cadmium wire approaches the inside diameter of the passive-wall tubular flow chamber. Thus an increase in reactor volume can only be achieved by increasing its length. This characteristic leads to unacceptable amounts sample dispersion (dilution and loss of analytical detection) and back pressure for batch analyzer applications may require reduction systems with liquid volume capacities of several milliliters.

There is a need for high reactive surface-to-volume ratios in cadmium reduction systems, that overcome the problems of low reactivity per unit length of single wire in tube and open tubular cadmium reactors while maintaining advantages of low flow resistance, and that eliminates the void areas and void volume formation problems, including compression, found in granular cadmium packed bed reactors. The present invention addresses this need.

SUMMARY OF THE INVENTION

The present invention includes a nitrate reduction device comprising a reactor having a flow chamber having a first end for receiving a nitrate sample and a cadmium containing structure forming a plurality of longitudinal channels within the flow chamber. Preferably, the cadmium containing structure comprises a plurality of wires.

The present invention also includes a nitrate analyzing apparatus comprising the nitrate reduction device.

Furthermore, the present invention includes a method for reducing nitrate to nitrite comprising the steps of providing a nitrate reduction device with a reactor having a flow chamber having a first end for receiving a nitrate sample and a plurality of cadmium containing wires located within the flow chamber, inputting nitrate sample into the flow chamber and cycling the nitrate sample within the flow chamber, where the nitrate reduces to nitrite.

The present invention provides for a resulting nitrite product that is preferably substantially complete.

DETAILED DESCRIPTION OF THE PREFERRED EMBODIMENT

The present invention provides a novel nitrate reduction device. The nitrate reduction device includes channels formed by cadmium structures, such as cadmium or cadmium alloy wires, within a reactor for reducing nitrate samples to nitrite. The present invention is used for batch-operated in situ, colorimetric nitrate monitors. Reproducible and high yield conversions of nitrate to nitrite are needed for proper analysis of the nitrate levels within an aqueous environment, such as a river, stream, lake or other water body. These conversions are used for chemical analysis for water quality studies, waste water monitoring, and other environmental monitoring applications.

The in situ monitoring application of nitrate becomes effective with high and constant nitrate reduction efficiencies for extended periods of time, such as a month or more. The cadmium reduction devices previously known failed to achieve constant or high reduction efficiencies or failed to maintain high or consistent reduction efficiencies over extended periods. With the use of multiple channels, i.e., high surface-to-volume ratios, the present invention provides a highly reactive, robust and simple nitrate reduction chamber for field use.

A representative reduction equation for nitrate to nitrite of the present invention is shown in equation 1, below:

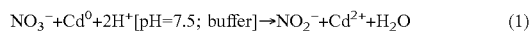

$$NO_3^- + Cd^0 + 2H^+ [pH=7.5; \text{buffer}] \rightarrow NO_2^- + Cd^{2+} + H_2O \quad (1)$$

Figure 1:
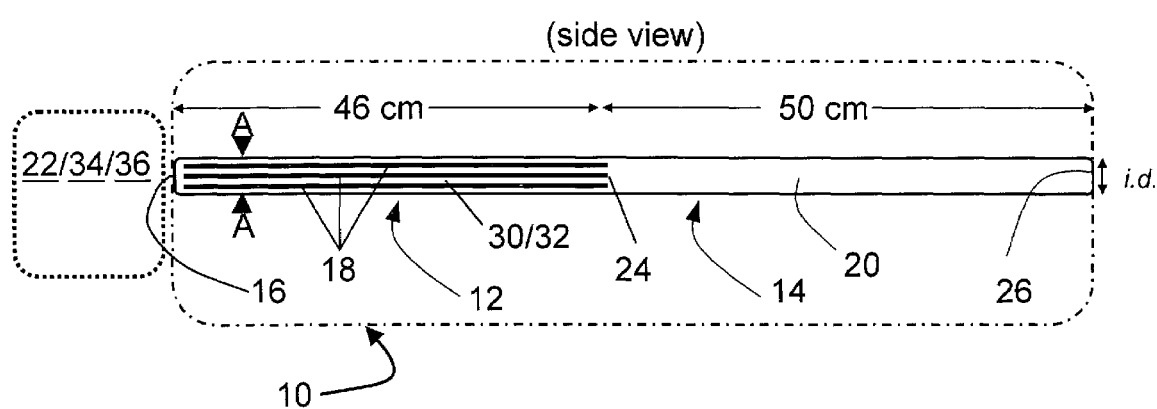
FIG. 1 shows a side view of the nitrate reduction device of the present invention.

As seen in FIG. 1, the nitrate reduction device 10 of the present invention comprises a reactor 12 with a flow chamber 14 having a first end 16 for receiving a nitrate sample and a cadmium containing structure, that preferably comprises a plurality of cadmium containing wires, 18 forming a plurality of longitudinal channels 30 within the flow chamber 14. The reactor 12 may comprise any appropriate material for encasing the cadmium containing structure that does not interfere with the proper reduction functioning. Representative structures included for example polymeric compositions such as polyethylene, polypropylene, etc., glass structures, metals such as stainless steel and the like. These structures provide non-reactive and water-tight encasements. Preferably, the reactor 12 is flexible and transparent for ease of handling, positioning and/or monitoring.

The reactor 12 includes the flow chamber 14 and cadmium surface for reducing nitrate. The flow chamber 14 comprises a contained environment having sufficient volume to encase, or totally contain, the cadmium wires 18 as the wires 18 are longitudinally grouped to form channels 30, with additional volume to receive and retain liquid sample 32 having a possible nitrate content. Preferably, the flow chamber 14 comprises a hollow, substantially longitudinal member of sufficient length to encase the wires 18, and more preferably has a length that additionally supports a buffer section 20. Representative dimensions of the flow chamber 14 include, for example, lengths of from about 10 cm to about 100 cm for the part of the flow chamber 14 that encases the wires 18, such as 20 cm, 46 cm, 56 cm, 72 cm and 88 cm, with additional length for the buffer section 20 of from about 10 cm to about 100 cm, such as 20 cm, 35 cm, 50 cm, 65 cm and 85 cm. The inner lining of the flow chamber 14 may be of any appropriate composition as determinable by one skilled in the art for the purposes described herein, and may include cadmium or a cadmium alloy such as cadmium plating.

The first end 16 of the flow chamber 14 preferably has a separate filtration unit or other means 22 for removing large contaminates from entering the flow chamber 14, such as twigs, dirt particles, sediment, mud, seeds, and other such objects. A fluid to be tested, generally being water, is introduced into the first end 16. The flow chamber 14 provides open flow communication between the flow chamber 14 and the buffer section 20. Preferably, the buffer section 20 is attached to the flow chamber 14 and located opposite, longitudinally, from the first end 16 of the flow chamber 14.

The buffer section 20 comprises a first open end 24 attached to the flow chamber 14 and a second open second end 26 that is open to the environment, such as being immersed in a lake or stream or vessel for waste stream collection. Contained within the buffer section 20 an appropriate amount of chemical buffer solution is maintained. The amount of chemical buffer solution includes that amount needed to "wash" an operational section of the wires 18 within the flow chamber 14 during operation, while ensuring that the wires 18 are always in contact with a liquid. This amount includes from about one-fifth of the length of the flow chamber 14 to about the full length of the flow chamber 14. Preferred amounts include enough chemical buffer solution to cover about all, three-fourths, two-thirds, one-half, one-third, one-fourth, etc. of the length of wires 18 in the flow chamber 14. The chemical buffer solution provides a pH environment on the wires 18 to enhance reduction of the nitrate by the cadmium upon and within the surface of the wires 18. The preferred pH environment of the wires 18 ranges from about 6.5 to about 8.5, and accordingly the chemical buffer solution preferably has a pH of from about 6.5 to about 8.5.

Chemical buffer solutions useful for cadmium reduction reactions preferably include imidazole (HNCHNCHCH), ammonium chloride ($NH_4Cl$) or combinations thereof, with other appropriate buffering compounds being determinable by those skilled in the art in light of the disclosure herein. The chemical buffer solution strongly complexes Cd (II) ions that otherwise would deactivate the cadmium by forming insoluble $Cd(OH)_2$ on the surface of the wires 18, i.e., the chemical buffer solution should complex cadmium (II) ions more strongly than hydroxide ions complex cadmium (II) ions. Additionally, the chemical buffer solution concentration needs to be sufficient to complex cadmium (II) ions formed not only by reaction of the cadmium with nitrate, but also from reaction of dissolved oxygen that may be present in concentrations typically ranging at 1000 times greater than nitrate. Copper ions, such as from copper sulfate, or other appropriate additions, such as silver, mercury and the like, are preferably added into the buffering solution to continuously activate the cadmium surface. Chemical buffer solutions are added to sufficiently complex cadmium ions, with non-limiting representative amounts of added chemical buffer solution being from about 1:9 to about 9:1, and the like, of sample to chemical buffer solution, respectively, with the proper amount of added chemical buffer solution being determinable by those of ordinary skill in the art in light of the disclosure herein. Typically chemical buffer solution concentrations (imidazole) include for example without limitation from about 0.05 molar to about 0.25 molar, such as about 0.1 molar, with appropriate amounts of other constituents included, as taught herein.

Figure 2:
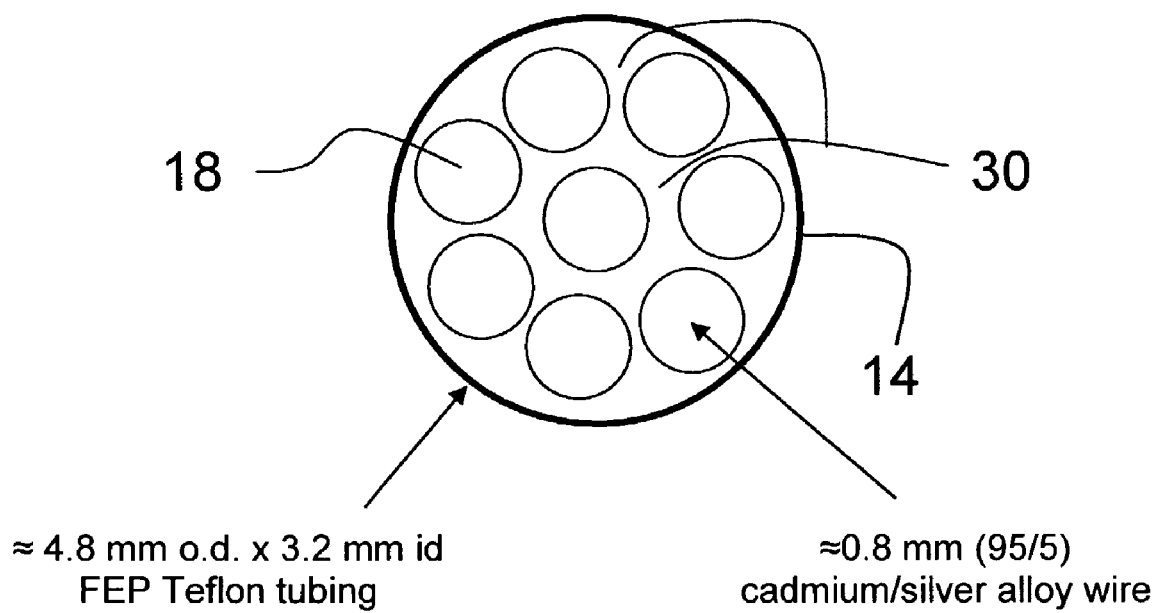
FIG. 2 shows a cross-section view of the nitrate reduction device of the present invention shown in FIG. 1 along A—A.

As further seen in FIG. 2, a cross-sectional view of FIG. 1 at position A—A, the cadmium containing structure 18 preferably comprises a plurality of wires 18 sufficient to create a high surface-to-volume ratio of the surface area of the cadmium surface and the void volume of the flow chamber 14. The structure 18 may include a single structure 18 with multiple longitudinal channels 30 therein or multiple wires 18 held, fused or tied together to form a longitudinal lattice. Preferably, the structure 18 comprises multiple independent wires 18 held as a single unit by the confines of the flow chamber 14, thus forming multiple channels 30 therebetween.

The wires 18 contain sufficient cadmium content along the surface area of wires 18 for effective reduction of the nitrate to nitrite. The cadmium content may include from about 80% cadmium to about 100%, with alloys of cadmium including copper, mercury and silver. Preferred cadmium alloy wires 18 include cadmium/silver alloy wires 18, with preferred relative amounts of cadmium and silver being from about 90% w/w to about 99.5% w/w cadmium and from about 10% w/w silver to about 0.5% w/w silver. Most preferably, the cadmium/silver content of the wires 18 comprises about a 95/5 ratio, as the 95/5 wires 18 generally maintain reactivity better than pure cadmium wires 18 and the 95/5 wires 18 provide a substantially stiffer composition that is easier to fabricate into a multi-strand configuration within the reactor 12. The surface of the wires 18 may have any texture, such as smooth or rough, with a rough surface preferred for facilitating reduction of the nitrate.

The number of cadmium containing wires 18 becomes best calculated by the resultant surface-to-volume ratio, with the number of wires 18 ranging from about 2 wires or greater, more preferably from about 5 wires to about 100 wires, and most preferably from about 8 wires to about 20 wires. The number of wires 18 preferably proportion the void volume of the flow chamber 14 to an amount of from about 20% to about 80%, preferably from about 50% to about 80%, of the total internal volume of the flow chamber 14 without the wires 18, e.g., the cross-sectional area of the cadmium wires 18 ranges for example from about 40% to about 80% of the total cross-sectional area of the flow chamber 14 (volume percentages remain the same as the lengths of the flow chamber 14 and wires 18 are equal).

The device may be automated by appropriate cycling means 34 or nitrate analyzing apparatus 36, either of which may move the nitrate sample within the flow chamber 14 in a suitable manner as determinable by one of ordinary skill in the art in light of the disclosure herein. Selection of a cycling means 34/36 may depend on the harshness of the operational environment of the nitrate reduction device 10, space limitations, sample frequency, cost and other such factors. Representative cycling means 34/36 include without limitation pumps and syringes. Typical cycling includes for example without limitation individual cycles of three to ten seconds with pauses of five to ten seconds repeated over a period of 30 seconds to ten minutes, such as about three minutes.

The nitrate reduction device 10 may be incorporated within a nitrate analyzing apparatus 36 for testing nitrate concentrations in open water bodies. Such devices include the EcoLAB manufactured by WS Envirotech of Selborne, Hants, United Kingdom, the NAS-2E manufactured by WS Envirotech of Selborne, Hants, United Kingdom and the AutoLAB manufactured by WS Envirotech of Selborne, Hants, United Kingdom.

Figure 3:
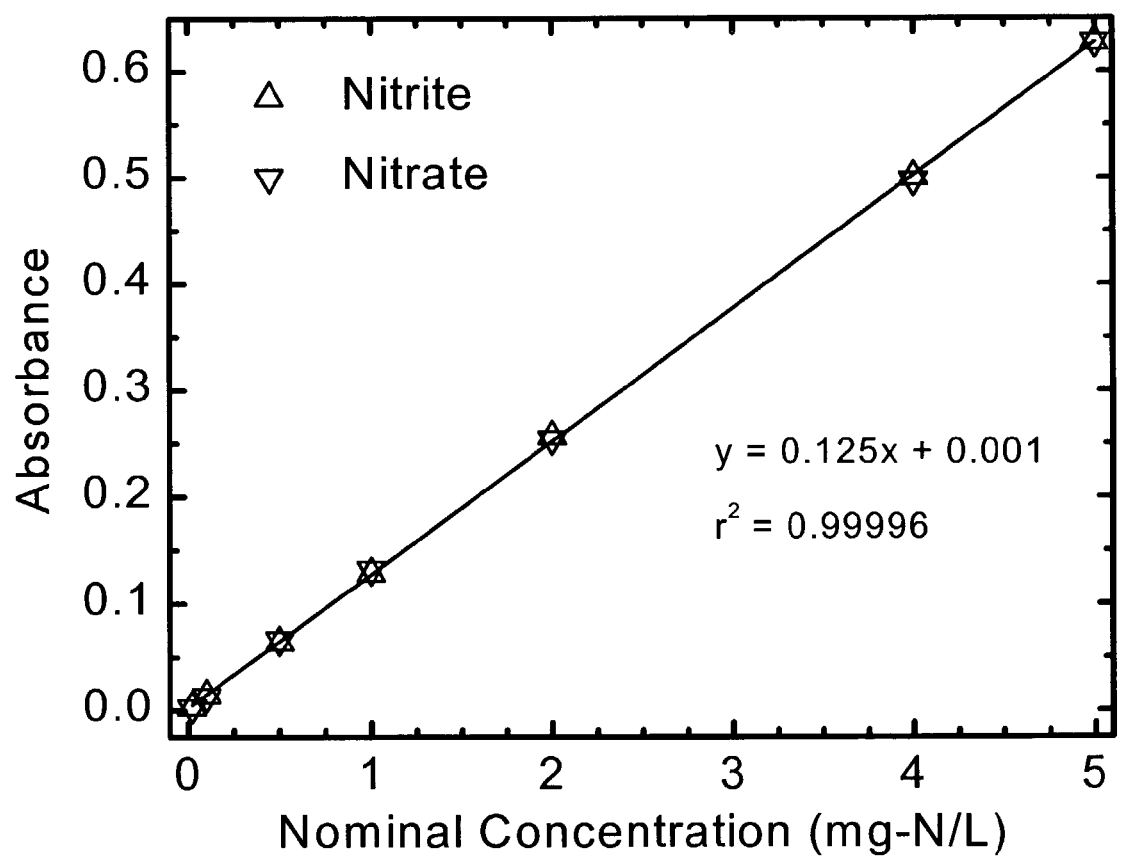
FIG. 3 shows a graph for the quantitative reduction of nitrate to nitrite with nominal concentration along the x-axis and absorbance along the y-axis of the present invention.
Figure 4:
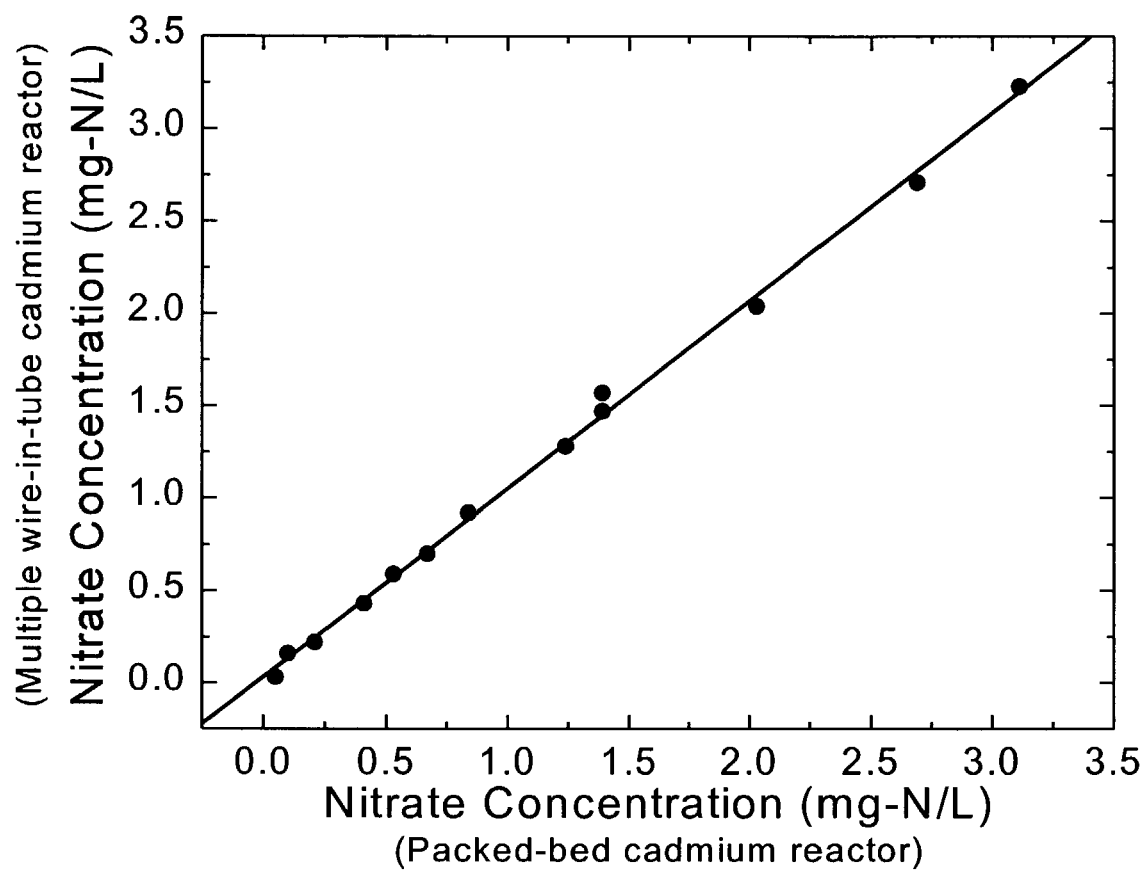
FIG. 4 shows a graph comparing the results of the nitrate reduction device of the present invention and a granular cadmium packed bed reactor for a natural water body with the nitrate reduction device of the present invention along the y-axis and a granular cadmium packed bed reactor along the x-axis.

FIG. 3 shows a graph for the quantitative reduction of nitrate to nitrite with nominal concentration along the x-axis and absorbance along the y-axis for the present invention. As seen in FIG. 3, near total conversion of nitrate to nitrite occurs. FIG. 4 shows a graph comparing the results of the nitrate reduction device of the present invention and a standard laboratory granular cadmium packed bed reactor for samples from natural water bodies with the nitrate reduction device of the present invention along the y-axis and a granular cadmium packed bed reactor along the x-axis. The results show an equivalence between the highly efficient granular cadmium packed bed reactor and nitrate reduction device 10, with the nitrate reduction devices 10 being more resilient to extended periods of use, e.g., avoiding void volume formation.

Figure 5:
FIG. 5 shows a diagram of the process for using the nitrate reduction device of the present invention.
Figure 5:

As seen in FIG. 5, in operation nitrate is reduced to nitrite using the nitrate reduction device 10 by a process that includes the steps of providing 100 the nitrate reduction device 10 with a reactor 12 having a flow chamber 14 having a first end 16 for receiving a nitrate sample and a plurality of cadmium containing wires 18 located within the flow chamber 14, inputting 102 nitrate sample into the flow chamber 14 and cycling 104 the nitrate sample within the flow chamber 14 in a manner effective to reduce the nitrate to nitrite.

Figure 6:
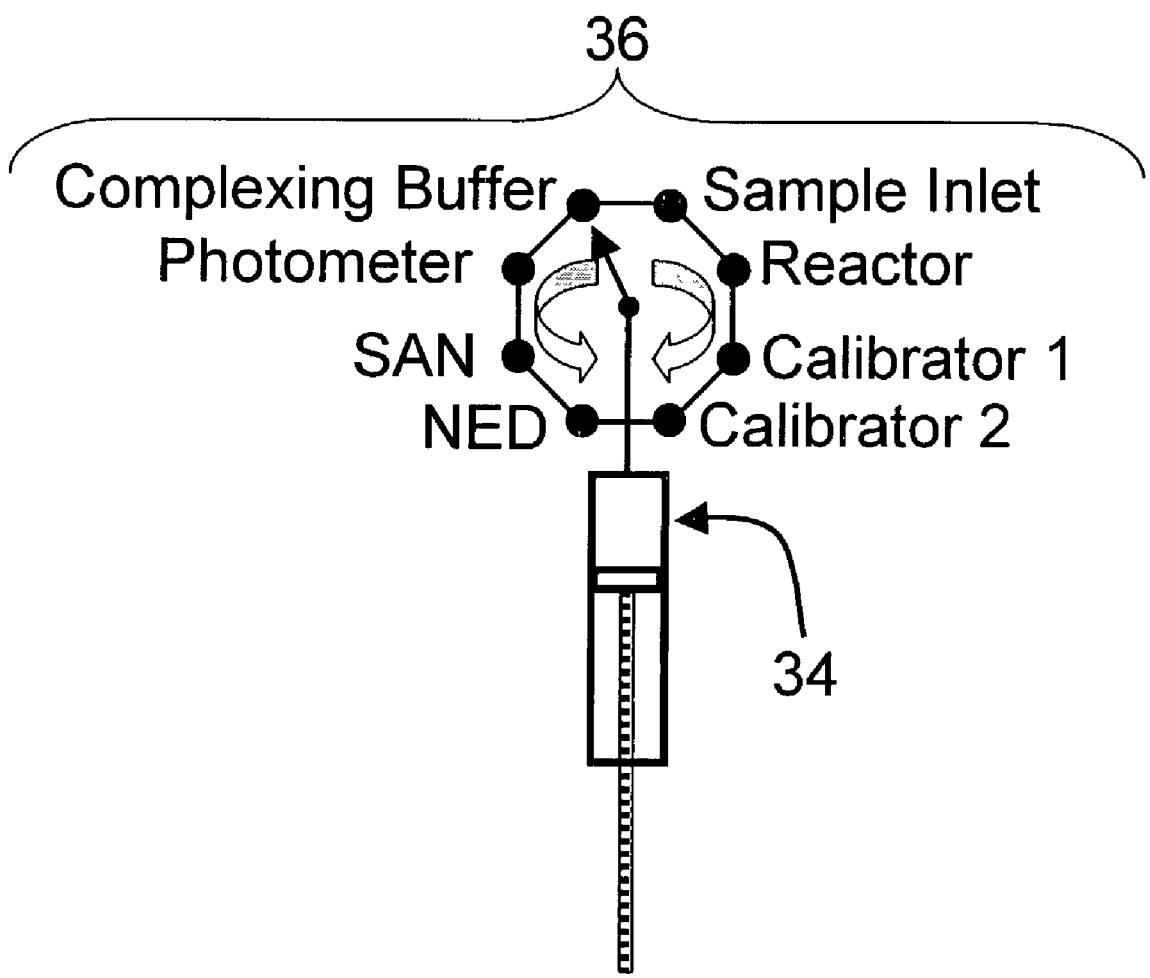
FIG. 6 shows a schematic of the nitrate reduction device attached to a nitrate analyzing apparatus for open environment testing; and, FIG. 7 shows a graph of the nitrate/nitrite levels of a natural water body.

Referring to FIG. 6, the nitrate reduction device 10, shown in FIG. 1, is attached at the "Reactor" position, or port. A sample is pulled from the environment through the port labeled "Sample Inlet" into a reservoir of the cycling means 34. Complexing buffer, such as for example imidazole, is additionally pulled into the reservoir of the cycling means 34 containing the sample. The contents of the reservoir are then mixed. The mixed sample/buffer is inserted into the reactor, where it is cycled in and out of the reactor, such as from about 1 to about 100 times, preferably about 10 times, until reduction of nitrate to nitrite is effectively complete. A volume of the reduced solution equivalent to 1 to 100 percent of the original volume of the inserted sample/buffer solution is withdrawn into the reservoir of the cycling means 34, with the withdrawn volume being preferably about 67 percent.

A first reagent such as sulfanilamide (SAN), then second reagent such as N-(1-Naphthyl)ethylenediamine (NED), are added to the withdrawn sample to create a color reaction. After waiting for the color reaction to reach a desired degree of completion, the reaction mixture is inserted into a photometric detector, at the "Photometer" port, and measured for the extent to which it absorbs light of an appropriate wavelength for detecting nitrite. Before another sample is received into the cycling means 34, the remnants of the previous sampling are discarded from the cycling means 34 and from reactor 10, followed by a rinsing of reactor 10 with chemical buffer solution. "Calibrator 1" and "Calibrator 2" contain known levels of nitrate solution for relating the absorbance of an unknown sample to a known concentration, with testing of the "Calibrator 1" and/or "Calibrator 2" being determinable by those skilled in the art. When either "Calibrator 1" or "Calibrator 2" contain a known nitrite solution, testing for completeness of the conversion process within the reactor 10 may be verified.

Figure 7:
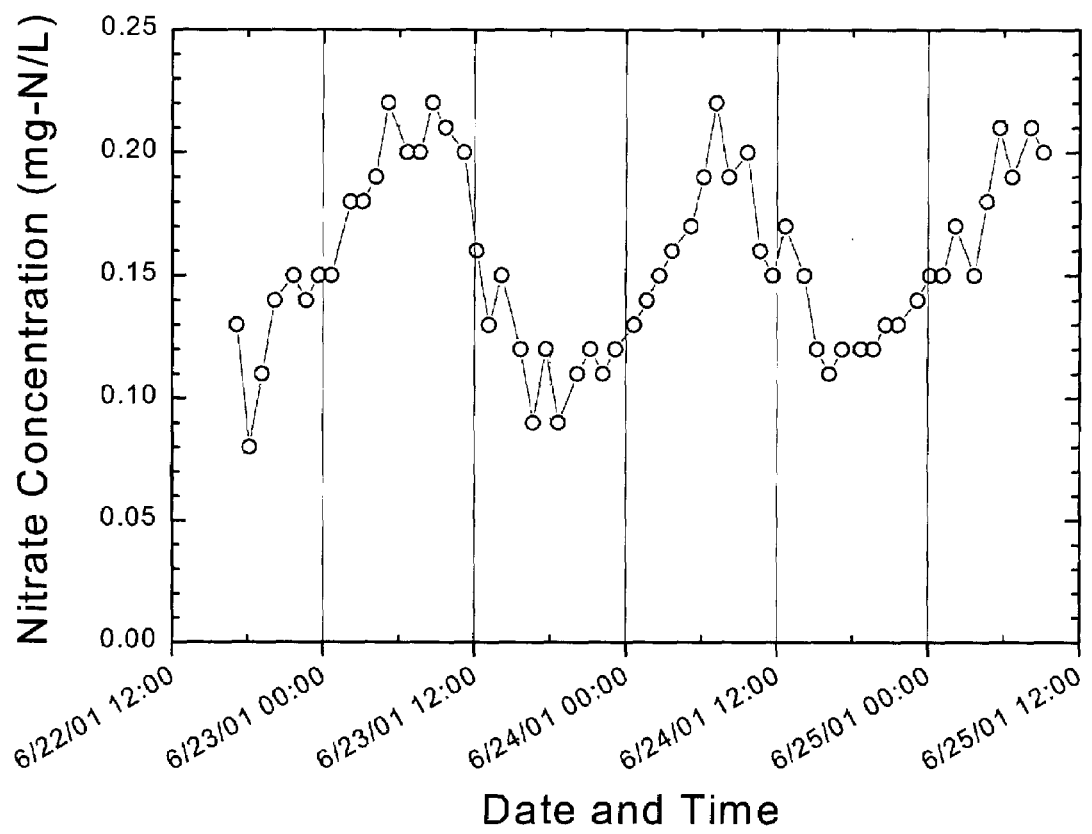

As seen in FIG. 7, the nitrate/nitrite concentration level of an open, e.g., natural, water body such as a stream varies with the time of day, having increased concentrations from 6 pm to 6 am and decreased concentrations from 6 am to 6 pm due to photosynthetic activity of aquatic plants in the stream.

With the reduction of a nitrate sample to nitrite, a final nitrite product is produced. The final nitrite product may result from partial or complete conversion of the nitrate sample as useful for any specified purposes. As natural water samples are routinely measured against standard solutions, total conversion of the nitrate to nitrite may not be necessary. For universal use, however, preferably the conversion is at least substantially complete, i.e., from about 97% or greater, and more preferably reduction occurs at about 100% of the nitrate as determinable within the experimental error of the detection limits of given analytical methods. Nitrate reduction device 10 may process fluids that contain no nitrate, i.e., containing concentrations less than the method detection limit including zero.

The nitrate reduction device 10 provides a flow-through, multi-strand, wire-in-tube, cadmium/silver alloy reduction device for nitrate determination within a sample. The reactor 12 may vary in size, such as being 5 cm in length and 2 mm i.d., containing a number of small diameter wires 18, such as 0.15 mm, and used for nitrate determinations by a variety of continuous flow analysis techniques including, but not limited to, air-segmented continuous flow analysis, flow-injection analysis, and sequential injection analysis.

The present invention is particularly applicable for long-term unattended experimental deployments in remote monitoring scenarios. In such environments, batch-operated in situ calorimetric nitrate monitors generally use intermittent insertion and withdrawal of buffered samples into and out of the reduction device where the nitrate is reduced to nitrite.

EXAMPLE 1 (Comparative)

Void Volume of Single Strand Wire (Willis Article)

A 1-meter length section of 1/16-inch (1.59 mm) i.d. Teflon tubing is threaded with a 1-meter length of 0.05-inch (1.27-mm) diameter cadmium wire. The surface-to-volume ratio equals 1.33 mm$^2$/microliter, with the cadmium volume wire equal to 785 mm$^3$.

By comparison, the liquid volume capacity of the single-wire-in-tube reactor for application in continuous flow analyzers described in the previously referenced Willis Article is about 0.7 milliliter. The novel multi-strand wire-in-tube reactors, which are the subject of the present invention, can be configured to accommodate larger solution volumes in relatively short flow chambers simply by increasing the cross section of the flow chamber and inserting more wires. Using this approach, low back pressures, high surface to volume ratios, and lower sample dispersion are achieved.

EXAMPLE 2

Void Volume of Multiple Strand, Wire-in-Tube Configurations

A 1-meter length section of 3.2-mm i.d. tubing is threaded with 8,1-meter lengths of 1-mm diameter cadmium/silver (95/5) wire. The surface-to-volume ratio equals 14.3 mm$^2$/microliter.

EXAMPLE 3

Void Volume of Multiple Strand, Wire-in-Tube Configurations

A 1-meter length section of 3.2-mm i.d. tubing is threaded with 8,1-meter lengths of 0.8-mm diameter cadmium/silver (95/5) wire. The surface-to-volume ratio equals 5 mm$^2$/microliter.

EXAMPLE 4

Void Volume of Multiple Strand, Wire-in-Tube Configurations

A 1-meter length section of 4 mm i.d. tubing is threaded with 10, 1-meter lengths of 1-mm diameter cadmium wire. The surface-to-volume ratio equals 6.7 mm$^2$/microliter.

EXAMPLE 5

Void Volume of Multiple Strand, Wire-in-Tube Configurations

A 1-meter length section of 5-mm i.d. tubing is threaded with 50,1-meter lengths of 0.5-mm diameter cadmium/silver (95/5) wire. The surface-to-volume ratio equals 8.0 mm$^2$/microliter.

EXAMPLE 6

Void Volume of Multiple Strand, Wire-in-Tube Configurations

A 1-meter length section of 6-mm i.d. tubing is threaded with 100,1-meter lengths of 0.5-mm diameter cadmium/silver (95/5) wire. The surface-to-volume ratio equals 18.2 mm$^2$/microliter.

EXAMPLE 7

Void Volume of Multiple Strand, Wire-in-Tube Configurations

A 1-meter length section of 10-mm i.d. tubing is threaded with 75,1-meter lengths of 1-mm diameter cadmium/silver (95/5) wire. The surface-to-volume ratio equals 12.0 mm$^2$/microliter.

EXAMPLE 8

Void Volume of Multiple Strand, Wire-in-Tube Configurations

A 1-meter length section of 3-mm i.d. tubing is threaded with 7,1-meter lengths of 1-mm diameter cadmium/silver (95/5) wire. The surface-to-volume ratio equals 14.0 mm$^2$/microliter.

EXAMPLE 9

Operational Use

A nitrate reduction device having a flow chamber length of about 46 centimeters (cm) and cross-sectional diameter of 3.2 millimeters has a buffer section about 50 centimeters in length and about 3.2 millimeters cross-sectional diameter. The flow chamber has 8 cadmium/silver alloy wires (95/5) longitudinally packed together with each wire having a length of about 46 centimeters. The nitrate reduction device is attached to an EcoLAB in situ nitrate analyzer and placed into or near to a body of water. When used outside of the body of water, an auxiliary pumping device is configured to bring water from the water body to the inlet of the EcoLAB in situ nitrate analyzer is used. This auxiliary pumping device is preferably encased in a secure housing for ensuring continuous operation, and may include for example 12 volt batteries for power.

Automated operation of the nitrate reduction device by the EcoLAB in situ nitrate analyzer included pulling a sample from the water body, which was then mixed with a imidazole complexing buffer solution at a concentration of 0.1 molar and a ratio of 1:4 of sample to complexing buffer solution, respectively. About 2 milliliters of the mixed sample/buffer was inserted into the reactor, where it was cycled in and out of the reactor for about 10 times with each individual cycle lasting about five seconds with a five second pause prior to the initiation of the following cycle, to reduce the nitrate to nitrite. A volume of the reduced solution of about 1.5 milliliters was withdrawn. Reagents SAN and NED were added to the withdrawn sample in amounts of about 0.1 milliliter and 0.1 milliliters, respectively. After a period of about 90 seconds, the resulting color reaction turned the reaction mixture to a pink color and the reaction mixture was inserted into a photometric detector to detect nitrite, which was measured at a wavelength of about 540 nm. Samples were taken every hour. Calibration solutions also were run hourly. The results are shown in FIG. 7.

The foregoing summary, description, and examples of the present invention are not intended to be limiting, but are only exemplary of the inventive features which are defined in the claims.

What is claimed is:

1. An in situ nitrate reduction device, comprising:
   a reactor with a flow chamber having a first end for receiving a nitrate sample; and
   a cadmium containing structure comprising a plurality of wires forming longitudinal channels within the flow chamber.

2. The device of claim 1, wherein the flow chamber comprises a hollow, substantially longitudinal member.

3. The device of claim 2, wherein the flow chamber further comprises a buffer section in open flow communication with the flow chamber, wherein the buffer section is located opposite the first end of the flow chamber.

4. The device of claim 3, wherein the buffer section comprises an open second end.

5. The device of claim 3, wherein the cadmium containing structure extends exclusively within the flow chamber.

6. The device of claim 3, wherein the buffer section comprises a chemical buffer solution.

7. The device of claim 6, wherein the chemical buffer solution provides a pH of from about 6.5 to about 8.5.

8. The device of claim 6, wherein the chemical buffer solution comprises imidazole, ammonium chloride or combinations thereof.

9. The device of claim 1, wherein the cadmium containing wires comprise cadmium/silver alloy wires.

10. The device of claim 9, wherein the cadmium/silver alloy wires comprise from about 90% w/w to about 99.5% w/w cadmium and from about 10% w/w silver to about 0.5% w/w silver.

11. The device of claim 1, wherein the plurality of cadmium containing wires comprises from about 2 wires or greater.

12. The device of claim 11, wherein the plurality of cadmium containing wires comprises from about 5 wires to about 100 wires.

13. The device of claim 12, wherein the plurality of cadmium containing wires comprises from about 8 wires to about 20 wires.

14. The device of claim 1, wherein the proportion of void volume of the flow chamber having the plurality of cadmium containing wires therein is from about 20% to about 80% of the total internal volume of the flow chamber without the wires.

15. The device of claim 1, further comprising a cycling means for moving the nitrate sample within the flow chamber.

16. A method for reducing nitrate to nitrite, comprising:
   providing an in situ nitrate reduction device comprising a reactor with a flow chamber having a first end for receiving a nitrate sample and a plurality of cadmium containing wires located within the flow chamber;
   inputting nitrate sample into the flow chamber; and
   cycling the nitrate sample within the flow chamber, wherein the nitrate reduces to nitrite.

17. An in situ nitrate reduction device, comprising:
   a reactor having a flow chamber with a first portion receiving a nitrate sample and a second portion;
   a cadmium containing section located within the first portion of the flow chamber and comprising a plurality of wires; and
   a buffer section located within the second portion of the flow chamber and being in open flow communication with the cadmium containing section,
   wherein the plurality of wires are contained exclusively within the cadmium containing section.

* * * * *